(12) United States Patent
Thornton

(10) Patent No.: US 6,920,674 B2
(45) Date of Patent: *Jul. 26, 2005

(54) BARE STENT SHIP AND CRIMP DEVICE

(75) Inventor: Sally C. Thornton, Marlborough, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 125 days.

This patent is subject to a terminal disclaimer.

(21) Appl. No.: 10/360,108

(22) Filed: Feb. 6, 2003

(65) Prior Publication Data
US 2003/0135970 A1 Jul. 24, 2003

Related U.S. Application Data

(63) Continuation of application No. 09/681,009, filed on Nov. 16, 2000.

(51) Int. Cl.$^7$ .............................................. B25B 27/00
(52) U.S. Cl. ............................ 29/270; 29/235; 29/282; 29/283
(58) Field of Search ......................... 29/270, 235, 282, 29/283, 272, 280; 606/139, 140, 194, 108

(56) References Cited

U.S. PATENT DOCUMENTS

| | | | | |
|---|---|---|---|---|
| 5,061,275 A | | 10/1991 | Wallsten et al. ................ 623/1 |
| 5,672,169 A | * | 9/1997 | Verbeek .......................... 606/1 |
| 5,783,227 A | * | 7/1998 | Dunham ..................... 425/318 |
| 5,992,000 A | | 11/1999 | Humphrey et al. ........... 29/516 |
| 6,024,737 A | * | 2/2000 | Morales .......................... 606/1 |
| 6,063,102 A | | 5/2000 | Morales ...................... 606/198 |
| 6,074,381 A | | 6/2000 | Dinh et al. ..................... 606/1 |
| 6,082,990 A | | 7/2000 | Jackson et al. .............. 425/517 |
| 6,092,273 A | | 7/2000 | Villareal ...................... 29/516 |
| 6,108,886 A | | 8/2000 | Kimes et al. ................. 29/280 |
| 6,352,547 B1 | | 3/2002 | Brown et al. ............... 606/198 |
| 6,360,577 B2 | | 3/2002 | Austin ......................... 72/402 |
| 6,387,117 B1 | | 5/2002 | Arnold et al. ............. 623/1.11 |
| 6,618,921 B1 | * | 9/2003 | Thornton ..................... 29/270 |

OTHER PUBLICATIONS

U.S. Appl. No. 09/404,986, filed Sep. 22, 1999, Brown et al.

* cited by examiner

Primary Examiner—Lee D. Wilson
(74) Attorney, Agent, or Firm—Vidas, Arrett & Steinkraus

(57) ABSTRACT

A stent container has a first wall at the proximal end and a second wall at the distal end. The first wall has an opening therethrough sized for receiving an uncrimped stent therethrough. The opening opens into a chamber which is reducible in size from a first enlarged size to a second reduced size. The chamber in the first enlarged size is sized for receiving an uncrimped stent therein. A plurality of bars extend from the first wall to the second wall. The bars are movable between a first position and a second position. The plurality of bars in the first position and the first and second walls define the periphery of the chamber in the enlarged size. The plurality of bars in the second position and the first and second walls define the periphery of the chamber in the reduced size. A stent disposed in the chamber may be reduced in size by reducing the chamber from the first enlarged size to the second reduced size.

34 Claims, 5 Drawing Sheets

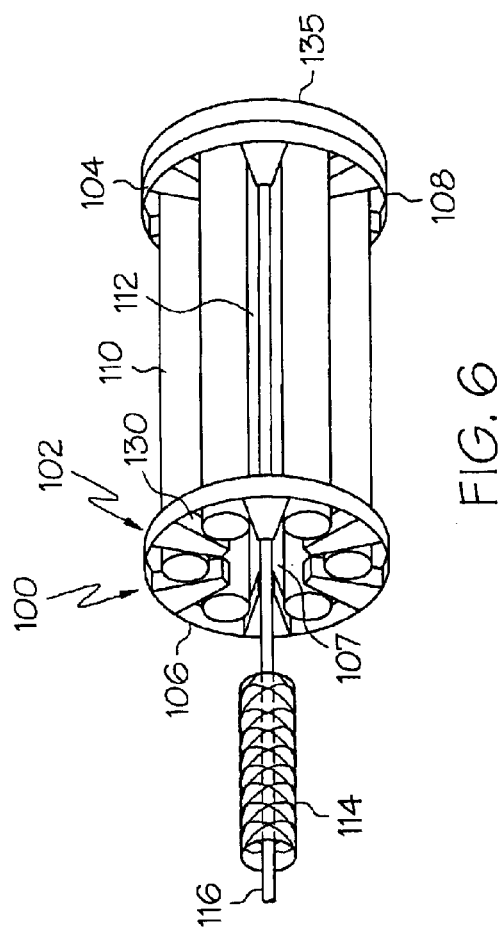
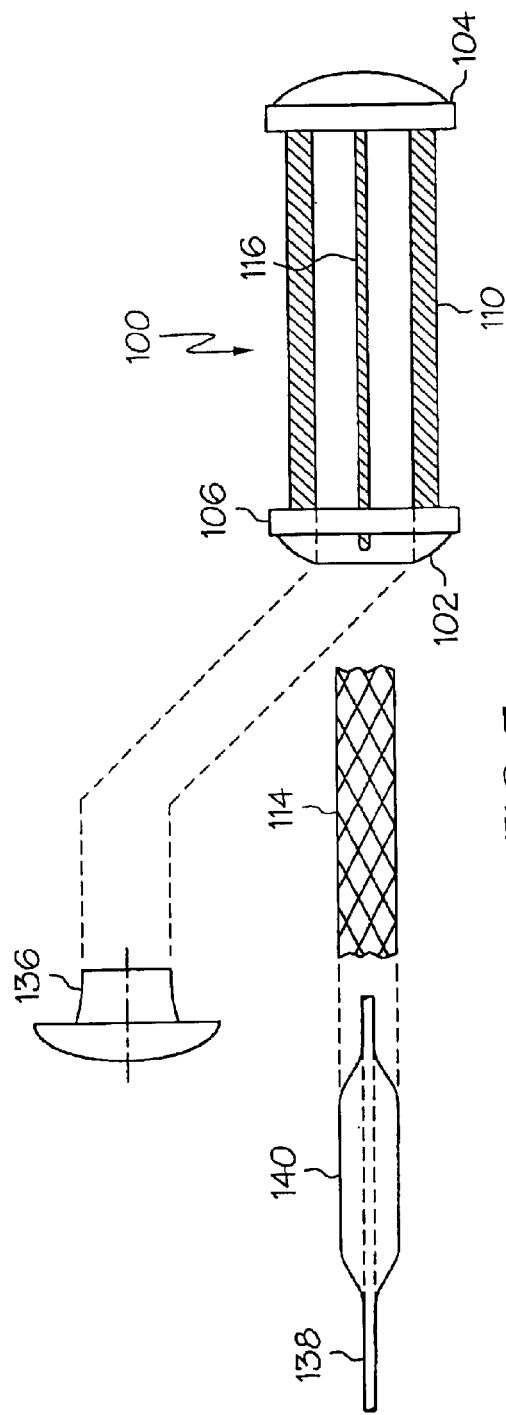

1

BARE STENT SHIP AND CRIMP DEVICE

CROSS REFERENCE TO RELATED APPLICATIONS

This is a continuation of U.S. patent application Ser. No. 09/681,009 filed Nov. 16, 2000 which is incorporated by reference herein in its entirety.

BACKGROUND OF THE INVENTION

A stent is a generally tubular device that is used to support a bodily lumen.

A stent is typically delivered to a desired bodily location via a catheter. In the case of a mechanically expandable stent such as a balloon expandable stent, the stent is disposed about the balloon and crimped to the balloon to prevent undesired movement of the stent relative to the balloon.

A number of techniques for crimping a stent to a balloon are used. One such technique that is commonly used in the radiological suite involves hand crimping the stent to the balloon. A stent is placed over an uninflated balloon and then squeezed with the fingers until the stent is in intimate contact with the uninflated balloon. The technique is highly operator dependent and can affect stent profile and stent placement with respect to the balloon and radiopaque markers. It can also affect the dilatation length of the stent and lead to pinching of the balloon.

Other techniques for crimping stents involve the use of mechanical devices for crimping stents. Mechanical stent crimpers have been disclosed in a number of patents including U.S. Pat. Nos. 6,108,886, 6,092,273, 6,082,990, 6,074,381, 6,063,102 and 5,992,000. Mechanical stent crimpers have also been disclosed in a number of copending, commonly assigned patent applications including U.S. application Ser. Nos. 09/401,467, 09/401,213, 09/404,986 and 09/401,218.

Typically, mechanical stent crimping devices are either used to crimp the stent to the catheter prior to shipping the stent or in the radiological suite. In the latter case, the radiologist selects a bare stent with the desired properties and then mechanically crimps the stent to the desired balloon catheter.

There remains a need for novel stent crimping devices that are capable of uniformly crimping a stent to a catheter and that may be employed at the point of use of the stent. There is also a need for stent crimping devices that may double as a shipping container for protecting the stent during shipping.

All US patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

The abstract provided herewith is intended to comply with 37 CFR 1.72 and is not intended be used in determining the scope of the claimed invention.

BRIEF SUMMARY OF THE INVENTION

The invention is directed to a stent container comprising a first wall at the proximal end of the container and a second wall at the distal end of the container. An opening is provided through the first wall. The opening, sized for receiving an uncrimped stent therethrough, opens into a chamber. The chamber is reducible in size from a first enlarged size to a second reduced size. In the first enlarged size, the chamber is sized for receiving an uncrimped stent therein. A plurality of bars extending from the first wall to the second wall, in conjunction with the first and second walls, define the chamber. The bars are movable between a first position and a second position. In the first position, the plurality of bars and the first and second walls define the periphery of the chamber in the enlarged size. In the second position, the plurality of bars and the first and second walls define the periphery of the chamber in the reduced size.

In one embodiment, the bars are movably received in the first and second walls. The first wall has a center and a plurality of slots disposed about the center. Each of the slots arcs toward the center with the bars movably received in the slots. The second wall has a plurality of radially disposed grooves therein, with the bars movably received in the grooves. The first wall is optionally rotatable relative to the second wall to move the bars from the first position to the second position and vice versa. The first and second walls may also be constructed such that the bars slide in a purely radially inward direction.

In another embodiment, the bars are flexible. The bars, disposed in the first and second walls and fixed to prevent radial movement, are capable of being flexed between the first and second positions to reduce a stent in size. The bars may optionally be rotatable.

The bars of the stent containers disclosed above are desirably spaced apart such that the stent is visible between adjacent bars to facilitate positioning the stent and any balloon to which the stent will be crimped therein. The bars may also be made of a transparent or translucent material to facilitate positioning.

The container may optionally have an uncrimped stent therein. The uncrimped stent may be reduced in size immediately upon insertion into the container, after one to two hours, one to two weeks, one to two months, six months or longer or any other suitable period of time.

The inventive container is constructed and arranged such that the chamber in the second reduced size is smaller than the uncrimped stent.

The invention is also directed to containers such as those described above where the chamber comprises a stent which has been reduced in size and optionally, crimped to a catheter.

The invention is also directed to a method of reducing a stent in size. In accordance with the method, a stent is provided in a container. The container has a first end wall and a second end wall and a plurality of bars extending between the first end wall and the second end wall. The first and second end walls and plurality of bars define a chamber in which the stent is received. The bars are movable between a first position in which they do not contact the stent to a second position in which they contact the stent and provide an inward force to the stent. The bars are in the first position when the stent is placed in the container. The bars may be moved from the first position to the second position thereby reducing the stent in size. Optionally, a medical balloon may be disposed within the stent prior to moving the bars and the stent crimped to the balloon. The stent may be reduced in size immediately upon insertion into the container or after a period of time such as at least one day, week, month, a half year or even years.

The invention is also directed to a method of reducing a stent in size using a coil. In accordance with the invention, a coil is disposed about a stent. The coil has a first end and a second end. The coil is reduced in diameter by moving at least one of the first and second ends of the coil relative to the other end so that the coil contacts the stent and applies an inward force to the stent sufficient to reduce the stent in size. The coil may be made of a suitable material such as a metal or polymer. Further in accordance with the method, a medical balloon catheter having a medical balloon portion may be provided. The stent may be disposed about the balloon portion of the medical balloon catheter prior to reduction of the stent in size. The coil may then be used to crimp the stent to the balloon.

In all embodiments of the invention where the stent is loaded onto a balloon, optionally a centering pin may be provided to guide the stent onto the balloon.

BRIEF DESCRIPTION OF THE SEVERAL VIEWS OF THE DRAWING(S)

FIG. 6 shows a side view of another inventive stent container;

FIG. 7 shows an exploded view of an inventive stent container including a cap;

DETAILED DESCRIPTION OF THE INVENTION

Figure 1:
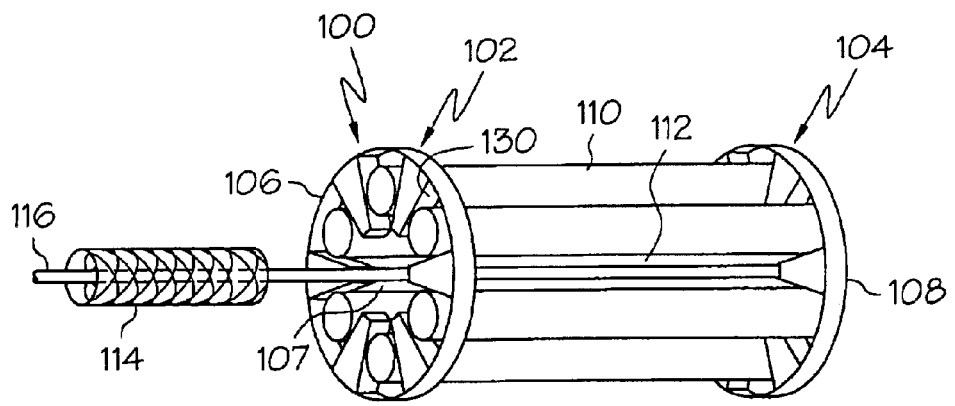
FIG. 1 shows a side view of an inventive stent container.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, like reference numerals in the figures refer to the same component. Also for the purposes of this disclosure, the term 'stent' shall refer to stents, grafts and stent-grafts. Finally, for the purposes of this disclosure, any references made to reducing a stent in size refer to a reduction in the transverse cross-section of the flowpath through the stent.

The instant invention, in one or more of its embodiments, is directed to devices which may be used to reduce stents in size and/or to store and ship stents. The devices may be used to reduce stents in size prior as a precursor to crimping the stent or as part of crimping the stent. The devices may also be used to reduce stents in size even where the stent is not subject to crimping. In certain embodiments, the device may serve as a container for storing and/or shipping the stent.

The invention is directed, in one embodiment to a device which may be used for crimping a stent and/or shipping a stent. As shown generally at 100 in FIG. 1, the device has a proximal end 102 and a distal end 104. First end wall 106 is located at the proximal end of the container and second end wall 108 is located at the distal end of the container. At least first end wall 106 has an opening 107 therein for receiving an uncrimped stent therethrough. A plurality of movable bars 110 extend from first wall 106 to second wall 108. The plurality of movable bars 110 define passage 112 therein sized for receiving uncrimped stent 114 therein. Opening 107 opens into passage 112.

Figure 2:
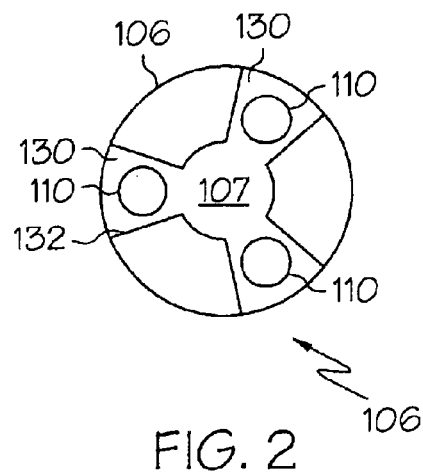
FIG. 2 shows an end view of an inventive stent container.
Figure 3:
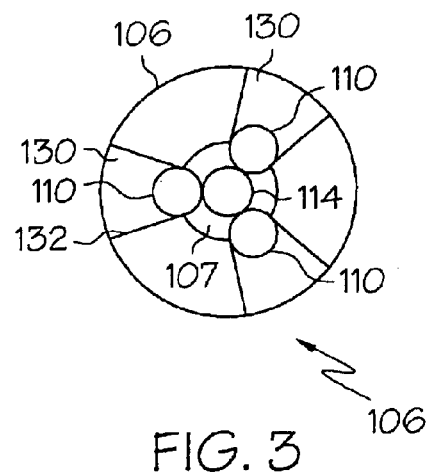
FIG. 3 shows an end view of an inventive stent container such as that shown in FIG. 2 with the bars partially engaging a stent.

First end wall 106 includes grooves or slots in which movable bars 110 are movably received. As shown in FIGS. 1 and 2, slots 130 may be radially disposed between adjacent spokes 132. Slots 130 taper inward as shown in FIG. 2. Spokes 132 may be made of a resiliently deform able material such as a polymeric material. An example of a suitable material is rubber. Absent any inward force applied to bars 110, bars 110 rest against spokes 132 and do not protrude into passage 112. With the application of force, spokes 132 may be deformed by bars 110 such that bars 110 protrude into passage 112 and apply a crimping force to a stent disposed therein, as shown in FIG. 3. FIG. 3 shows the stent in transverse cross-section. The end wall of FIGS. 2 and 3 have three slots and three spokes and may accommodate three bars 110. The end wall may have additional or fewer slots and spokes. An end wall corresponding to that of FIG. 1 has eight slots and spokes and accommodates eight bars. The inventive device may have as few as a single slot or may have any number of slots between two and twenty or more.

Figure 4:
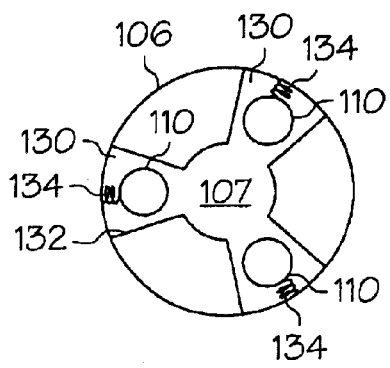
FIG. 4 shows an end view of an inventive stent container with spring-loaded bars.
Figure 5:
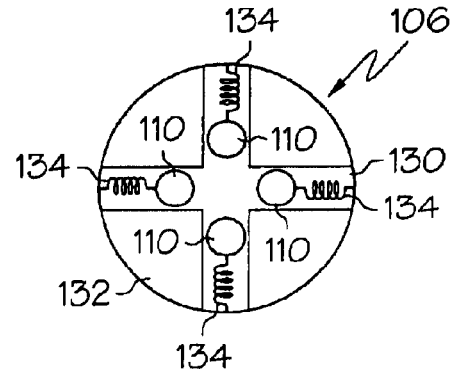
FIG. 5 shows an end view of another inventive stent container with spring-loaded bars.

In another embodiment, as shown in FIGS. 4 and 5, end wall 106 may optionally be provided with springs 134 or other coupling devices in communication with bars 110 to prevent bars 110 from contacting the stent until sufficient force is applied to the bars. Slots 130 as shown in FIG. 5 are of a constant width. Springs may be used in any of the other embodiments as well.

Other coupling devices such as a strip of stretchable material, for example rubber or other polymeric material, may also be used to prevent the bars from contacting the stent until sufficient force has been applied thereto in any of the embodiments disclosed herein employing bars.

Second end wall 108 may be of identical construction to first end wall 106 or may be of different construction. As an example of the latter, second end wall 108 may be closed so that no opening is provided therein for the stent.

First end wall 106 and second end wall 108 may be made of any suitable material including metal and polymeric materials. The first and second walls may be of solid construction or may have a plurality of openings therein shaped to receive movable bars 110 therein.

Movable bars 110 may be made of any material including metals such as stainless steel, where suitable, and polymeric materials. Desirably, the movable bars will be made of a smooth material. More desirably, the movable bars will be made of a lubricous material such as polytetrafluoroethylene.

Moveable bars may have a rectangular cross-section or more generally a polygonal cross-section or a curvilinear cross-section. Desirably, the cross-section will be circular.

The device may be provided in an embodiment in which the bars do not rotate about the stent.

The device may also be provided in an embodiment in which the bars may rotate about the stent. Such an embodiment is shown generally at 100 in FIG. 6. In the embodiment of FIG. 6, centering pin 116 extends from base 135, through an opening in second end wall 108 and into passage 112. Centering pin 116 maybe used to immobilize the stent or stent and catheter. Second end wall 108 is rotatably coupled to base 135 so that second end wall 108 and bars 110 may be rotated relative to centering pin 116. Any suitable rotatable coupling may be used. Desirably, bars 110 will have a circular cross-section.

Figure 10:
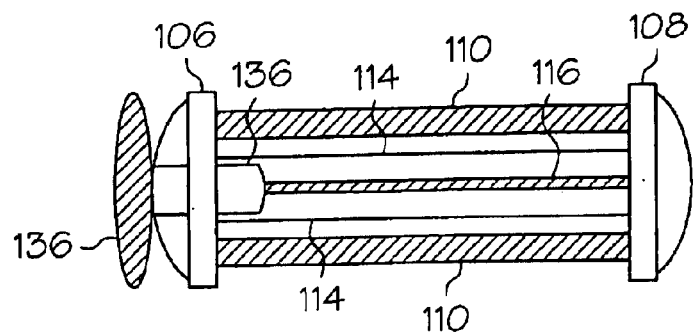
FIG. 10 shows an inventive stent container with a cap therein.

The inventive devices, in any of the above embodiments and embodiments below which employ bars, may further be provided with a cap 136 to close opening 107 in first end wall 106 as shown in FIGS. 7 and 10. A cap may also be provided to any close opening in the second side wall. Any suitable design may be used. The cap is of particular use to retain the stent in the device where the device is used for storage and/or shipping of the stent. The cap may have small openings therethrough to allow for the insertion of gas or evacuation of gas from the passage or chamber in which the stent resides.

Figure 8:
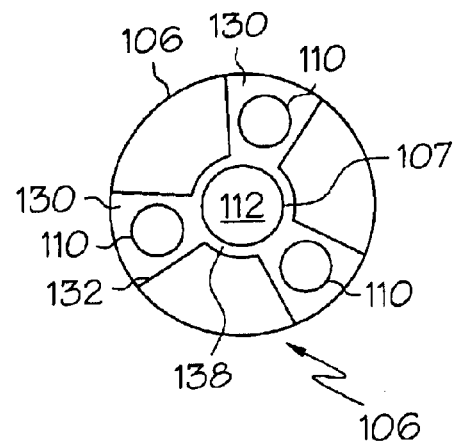
FIG. 8 shows an end view of an inventive stent container with an elastic membrane.

The device may further be provided with an elastic membrane 138 or otherwise deformable membrane disposed interior to the bars in passage 112 as shown in FIG. 8. The membrane may be secured to the bars and/or end walls and disposed between the bars and the stent to prevent direct contact between the bars and the stent. Suitable materials for the membrane include PTFE, rubber and SILASTIC®. Other polymeric materials may also be used.

Figure 9:
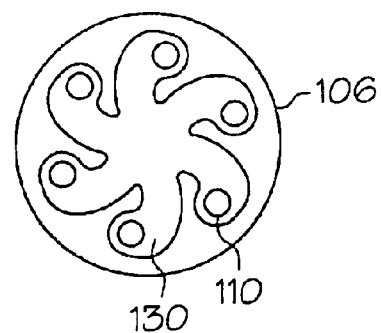
FIG. 9 shows an end wall of an inventive stent crimper with arcing slots.

The inventive device may also be provided in an embodiment wherein at least one of the end walls, as shown in FIG. 9, is provided with grooves or slots 130 that arc inward. The other end wall may be provided with like slots or with radial slots. The device of FIG. 9 is operable to reduce a stent in size by rotating the one or more end walls with the arcuate slots causing the bars to be pushed inward.

In use, an uncrimped stent is received in passage 112 and shipped in container 100 which is closed by end cap 136 or any other suitable closure device. Stent 114 may optionally be held in place by an end cap such as that shown in FIGS. 7 and 10 which fits in opening 107 and wedges stent 114 in place or fits loosely into stent 114. The stent may optionally be held in place by centering pin 116. The device may also be designed to be only slightly longer than the stent housed therein, to house the stent with little movement of the stent.

As discussed below, the stent optionally may be sterilized within the device.

The device may be used to prereduce a stent in size or to crimp a stent to a delivery catheter. In the former case, at the point of use, bars 110 may be pressed inward to apply a crimping force to the stent. In those embodiments where the bars are rotatable relative to the stent, the bars may be rotated about the periphery of the stent.

In the latter case, the cap, if present is removed and a catheter inserted in the device, interior to the stent. The stent may then be crimped by applying a force to the bars and, where applicable, rotating the bars about the stent. Typically, the stent will be crimped to a catheter balloon and catheter.

Figure 11:
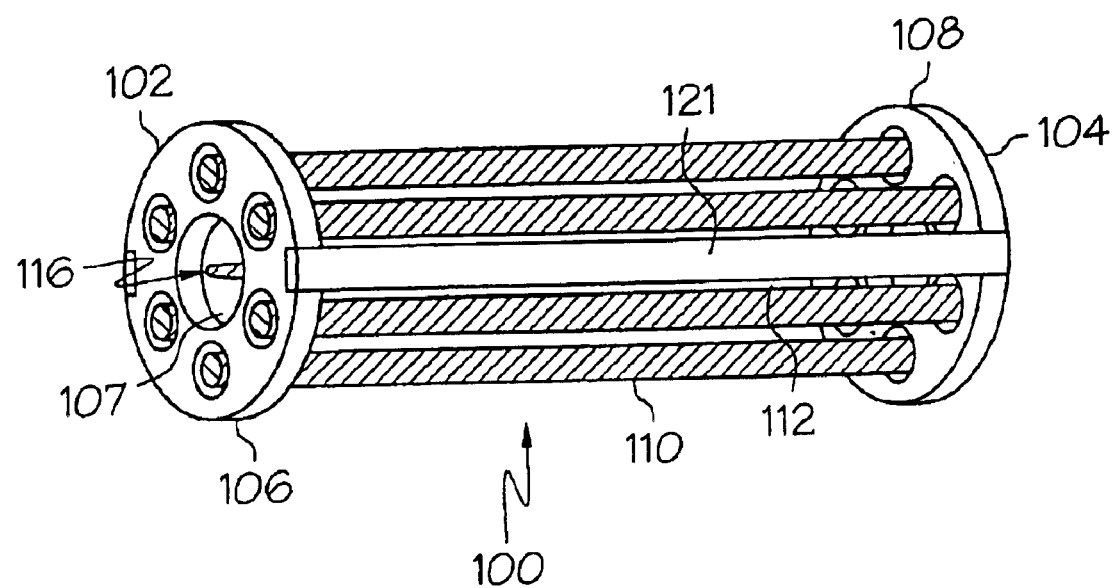
FIG. 11 shows an inventive stent container with flexible bars.
Figure 12:
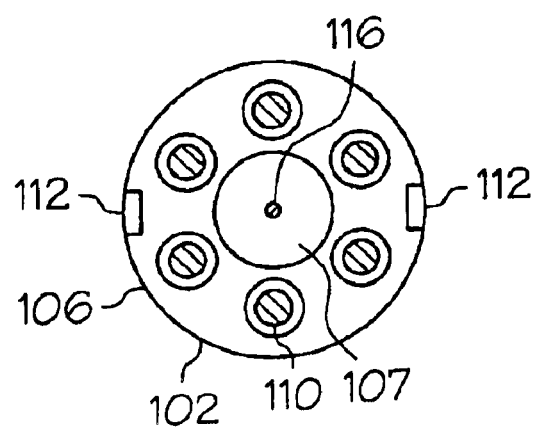
FIG. 12 shows a front end view of the inventive stent container of FIG. 11.

In another embodiment, the invention is directed to a device shown generally at 100 in FIG. 11. Stent container 100 has a proximal end 102 and a distal end 104. First end wall 106 is located at the proximal end of the container and second end wall 108 is located at the distal end of the container. At least first end wall 106 has an opening 107 therein for receiving an uncrimped stent therethrough. A plurality of flexible bars 110 extend from first wall 106 to second wall 108. Six such bars are shown in FIG. 11. The invention also contemplates embodiments in which additional or fewer bars are present. The plurality of flexible bars 110 define passage 112 therein sized for receiving an uncrimped stent (not shown) therein. Opening 107 opens into passage 112. Centering pin 116 is disposed in passage 112 and may optionally extend out opening 107. In use, the stent and optionally a catheter tube, typically the inner tube of a catheter are disposed about centering pin 116.

First end wall 106 and second end wall 108 may be made of any suitable material including metal and polymeric materials. The first and second walls may be of solid construction or may have a plurality of openings therein shaped to receive flexible bars 110 therein. In either case, flexible bars 110 may be adhesively secured, laser welded or otherwise welded, or otherwise secured to the first and second end walls.

Flexible bars 110 may be made of any material which may be flexed including metals such as stainless steel and polymeric materials. Desirably, the flexible bars will be made of a smooth material which may be easily flexed by hand. More desirably, the flexible bars will be made of a lubricous material such as polytetrafluoroethylene.

Device 100 may further comprise one, and desirably, a plurality of support bars 121 to maintain the integrity of the device. Support bars 121 may be made of any rigid material whether metal, polymeric or otherwise. Support bars 121 desirably are constructed and arranged so that they provide extra support during shipping and handling and may then be broken away or otherwise removed before or during reduction of the stent in size. For example, support bars 121 may be slidably removed from device 100 at the point of use. Support bars 121 may also be attached to device 100 via a frangible adhesive. The bond between support bars 121 and device 100 may then be broken at the point of use.

Any of the inventive devices described above may be provided in an embodiment where each of the individual bars may also be rotatably mounted in the end walls so that each bar rotates about its longitudinal axis even as the collection of bars rotates about the stent. Thus, for example, when applying a stent reduction force, each bar may be rotated about its longitudinal axis so that the bars are in rolling contact with the stent.

Any of the inventive devices disclosed above may be constructed such that the stent and the portion of any balloon catheter within the container are visible from outside the container. This may be accomplished by leaving gaps between bars and/or by providing bars of translucent or transparent material. Because of the visibility afforded the user, the stent may be aligned with the balloon or any radiopaque markers disposed on the catheter.

In use, an uncrimped stent is received in passage 112 of the container of FIG. 11 and, optionally, stored and shipped in container 100. Stent 114 may be held in place by an end cap, such as that shown for example in FIGS. 7 and 10 which fits in opening 107 and wedges the stent in place. The container may also be designed to be only slightly longer than the stent housed therein, to house the stent with little movement of the stent. Centering pin 116 may be provided in stent 114 to center the stent and optionally support the stent in the container.

Figure 13:
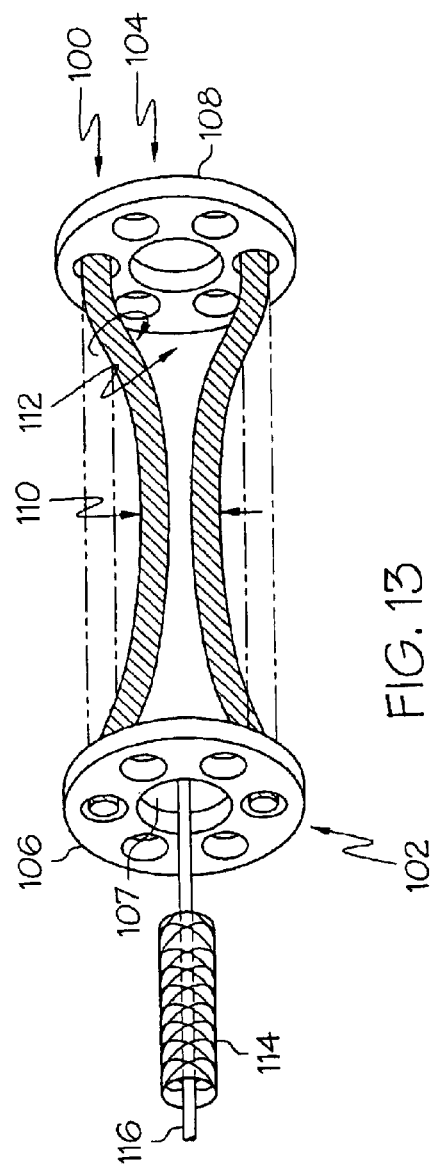
FIG. 13 shows a schematic illustration of an inventive stent crimper with some of the bars flexed.

When it is desired to reduce the stent in size, bars 110 may be flexed inward, as shown in FIG. 13 until they contact stent 114 and apply a inward force to the stent, thereby reducing it in size.

To crimp the stent to a suitable balloon catheter, the container may be opened where necessary and the balloon portion of a balloon catheter inserted therein. Stent 114 is aligned on the balloon and crimped thereto by flexing bars 110 inward, as shown in FIG. 13 until they contact stent 114 and apply a inward crimping force to the stent.

In another embodiment, the invention is directed to a method of reducing a stent in size using a coil and to inventive devices for accomplishing the same. A device for storing a stent and reducing a stent in size is shown generally at 200 in FIG. 14. Device 200 comprises a first wall 106 and a second wall 108 joined to the first wall via one or more connectors 121 extending between the walls. Any suitable connectors may be used including rods and/or bars and/or sheets of material extending from the first wall to the second wall. Desirably, the one or more connectors form an enclosed and optionally sterilizable housing. To that end, the one or more connectors may comprise a transparent or semi-transparent material or may include a window to facilitate positioning a balloon relative to the stent. Suitable sterilizable materials are discussed below.

Device 200 further comprises a coil 210 in which a stent may be disposed. First end 212 of coil 210 extends from first wall 106 at proximal end 102 of device 200. First wall 106 includes an opening 107 for receiving a stent therethrough. Opening 107 extends into stent receiving chamber 112. Second end 214 of coil 210 extends from second wall 108 at distal end 104 of device 200. Optional centering pin 116 extends from second wall 108 of device 200 and may be used to facilitate positioning the balloon catheter within the coil. At least one of first wall 106 and second wall 108 is movable relative to the other. Upon moving one of walls 106 and 108 away from the other wall, the diameter of the coil is reduced and coil 210 may apply sufficient force to a stent disposed in chamber 112 to reduce the stent in size.

Figure 14:
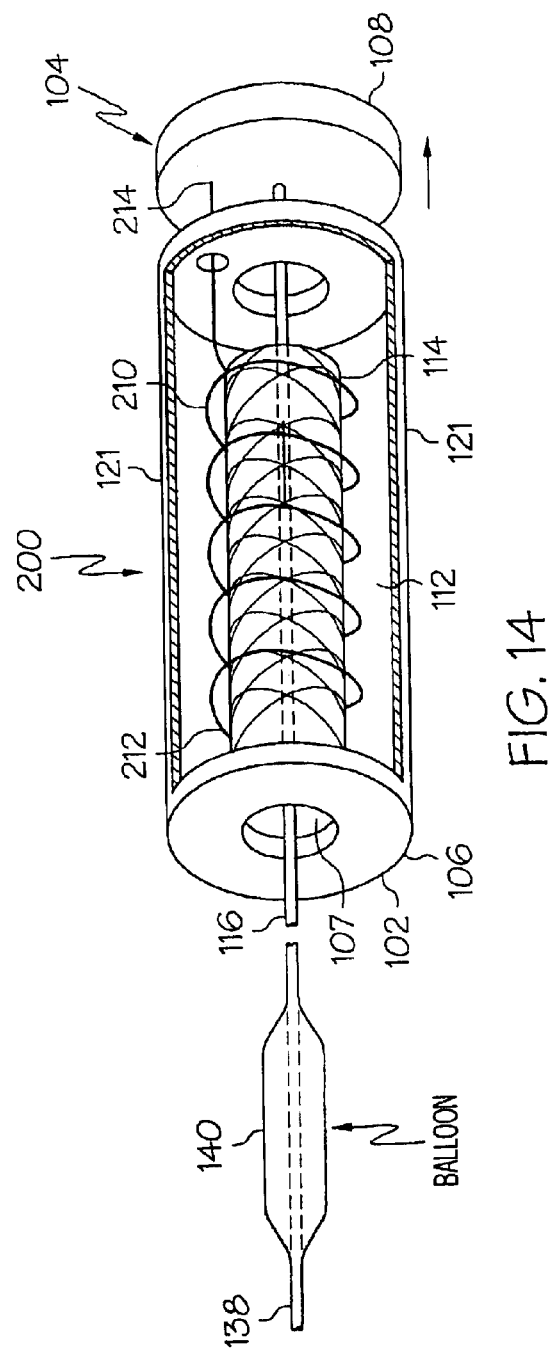
FIG. 14 shows another inventive stent container.

In accordance with the inventive method, as shown in FIG. 14, stent 114 is disposed within coil 210 of device 200. Balloon portion 140 of medical balloon catheter 138 is disposed within coil 210. Optional centering pin 116 extending from distal end wall 108 of device 200 may be used to facilitate positioning the balloon catheter within the coil. At least one of first end 212 and second end 214 of coil 210 is moved relative to the other thereby reducing the coil in diameter. As the ends are moved relatively further apart, the coil contacts the stent and reduces it in size, crimping the stent to the balloon. In one embodiment of the invention, one of the two ends is fixed in place and the other of the two ends is moved relative to the end which is fixed in place. In another embodiment, both ends are pulled apart. The inventive method may also be practiced in the absence of a balloon catheter for reducing a stent in size.

Coil 210 may be provided at one or both ends with a suitable gripping device to facilitate holding the ends of the coil and pulling the coil by hand. One or both ends may also be provided with a mechanical device capable of providing a mechanical advantage such as a screw to apply a constant force to one or both ends of the coil.

Coil 210 may be made of any suitable resilient material including metals and polymeric materials. Desirably, the coil is made of a material such as spring metal.

In another embodiment, the invention is directed to a stent container in which a braided stent such as a Wallstents® available from Boston Scientific Corporation and described in U.S. Pat. Nos. 5,061,275, 5,992,000, a finger prison or a tube which is reducible in size such as that disclosed in U.S. Pat. No. 5,992,000 is used to reduce a stent in size. The device may be mounted in a housing similar to that shown in FIG. 14, with a braided stent, finger prison or reducible tube mounted at one end to first wall 106 and at the other end to second wall 108. A stent may be reduced in size by moving at least one of the first and second walls away from the other wall.

The above described inventive devices may further be provided with an elastic membrane or otherwise deformable membrane inside the coil, Wallstent, finger prison or tube. Additional details of the elastic membrane are discussed above.

The inventive devices as disclosed herein may be constructed to be sterilizable prior to or once the stent is stored therein. In such case, it is desirable that the material from which the device is constructed be resistant to gamma radiation so that the device contents may be sterilized with gamma radiation. Suitable materials include treated polycarbonates such as Lexan™, Cycolac™, Valox™, Noryl™ and Ultem™. The exact choice of materials will depend on how the device is to be sterilized.

The invention contemplates reducing stents in size immediately after having been placed in any of the inventive devices disclosed herein and reducing stents in size that have been residing in the inventive device for periods of time ranging from one to two hours, to six months or more. A stent may be placed in any of the inventive devices and stored and/or shipped therein and then crimped or reduced in size after a week, a months, two month, half a year or longer, desirably at the point of use.

The invention is directed to methods of using the inventive disclosed herein wherein the devices are used to store the stents for periods of time ranging from one to two days, one to two weeks, one to two months and up to six months or longer.

The invention is also directed to any of the inventive devices disclosed above further comprising a stent which has been stored therein for a period of at least one to two days, one to two weeks, one to two months and as long as six months, a year or more.

In addition to the specific embodiments claimed below, the invention is also directed to other embodiments having the features of the independent claims and any other possible combination of the dependent features claimed below.

The above disclosure is intended to be illustrative and not exhaustive. The description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent container having a proximal end and a distal end comprising:

a first wall at the proximal end and a second wall at the distal end, the first wall having an opening therethrough sized for receiving an uncrimped stent therethrough and opening into a chamber, the chamber reducible in size from a first enlarged size to a second reduced size, the chamber in the first enlarged size sized for receiving an uncrimped stent therein;

a plurality of bars extending from the first wall to the second wall, the bars movable between a first position and a second position, the plurality of bars and the first wall and the second wall defining the periphery of the chamber, the plurality of bars constructed and arranged to contact the uncrimped stent and apply a force thereto upon movement of the bars from the first position to said the second position;

2. The stent container of claim 1 wherein the plurality of bars is movably received in the first and second walls.

3. The stent container of claim 2 comprising an uncrimped stent therein.

4. The stent container of claim 3 wherein the uncrimped stent has resided in the container for at least one week.

5. The stent container of claim 3 wherein the uncrimped stent has resided in the container for at least one month.

6. The stent container of claim 3 wherein the uncrimped stent has resided in the container for at least one half year.

7. The stent container of claim 3 wherein the chamber in the second reduced size is smaller than the uncrimped stent.

8. The stent container of claim 2 wherein the chamber is in the second reduced size.

9. The stent container of claim 8 wherein the chamber comprises a stent which has been reduced in size.

10. The stent container of claim 1 wherein the bars are flexible and are movable between the first and second positions by flexing.

11. The stent container of claim 10 comprising an uncrimped stent therein.

12. The stent container of claim 11 wherein the uncrimped stent has resided in the container for at least one week.

13. The stent container of claim 11 wherein the uncrimped stent has resided in the container for at least one month.

14. The stent container of claim 11 wherein the uncrimped stent has resided in the container for at least one half year.

15. The stent container of claim 11 wherein the chamber in the second reduced size is smaller than the uncrimped stent.

16. The stent container of claim 10 wherein the chamber is in the second reduced size.

17. The stent container of claim 16 wherein the chamber comprises a stent which has been reduced in size.

18. The stent container of claim 10 wherein the flexible bars are made of a smooth material.

19. The stent container of claim 18 wherein the material is stainless steel.

20. The stent container of claim 18 wherein the material is polytetrafluoroethylene.

21. The stent container of claim 1 wherein the bars are spaced apart such that the stent is visible between adjacent bars.

22. The stent container of claim 1 wherein the flexible bars are made of a transparent or translucent material.

23. The stent container of claim 1 further comprising a balloon catheter, the balloon catheter including a medical balloon, the medical balloon disposed within the stent.

24. A method of reducing a stent in size comprising the steps of:
providing a stent in a container, the container having a first end wall and a second end wall and a plurality of bars extending between the first end wall and the second end wall, the end wall and a plurality of bars extending between the first end wall and the second end wall, the first and second end walls and plurality of bars defining a chamber in which the stent is received, the bars movable between a first position in which they do not contact the stent to a second position in which they contact the stent and provide an inward force to the stent, the bars in the first position;
moving the bars from the first position to the second position thereby reducing the stent in size.

25. The method of claim 24 further comprising the step of disposing a medical balloon within the stent prior to moving the bars.

26. The method of claim 24 wherein a period of time of at least one day elapses between the providing step and the moving step.

27. The method of claim 24 wherein a period of time of at least one week elapses between the providing step and the moving step.

28. The method of claim 24 wherein a period of time of at least one month elapses between the providing step and the moving step.

29. The method of claim 24 wherein a period of time of at least one-half year elapses between the providing step and the moving step.

30. The method of claim 24 wherein the bars are moved from the first position to the second position by flexing the bars.

31. The method of claim 24 wherein the bars are moved from the first position to the second position by sliding the bars.

32. In combination, a stent container with a stent disposed therein, the stent container having a chamber defined by three or more movable bars extending between a first wall and a second wall, the bars movable inward toward one another,
the first wall having an opening therethrough sized for receiving a stent therethrough and opening into the chamber, the stent disposed in the chamber, the bars constructed and arranged such that the chamber is reducible in size from a first enlarged size to a second reduced size as the bars are moved inward, the plurality of bars and the first wall and second wall defining the periphery of the chamber.

33. The stent container of claim 32 wherein said bars are constructed and arranged to contact the stent and apply an inward force to the stent as they move inward.

34. A stent container having a proximal end and a distal end comprising:
a first wall at the proximal end and a second wall at the distal end, the first wall having an opening therethrough sized for receiving an uncrimped stent therethrough and opening into a chamber, the chamber reducible in size from a first enlarged size to a second reduced size, the chamber in the first enlarged size sized for receiving an uncrimped stent therein;
a plurality of bars each bar having a center, said bars extending from the first wall to the second wall movable between a first position and a second position with the entirety of the center being displaced, the plurality of bars and the first wall and the second wall defining the chamber.

* * * * *